United States Patent [19]
Sekiguchi et al.

[11] Patent Number: 5,571,679
[45] Date of Patent: Nov. 5, 1996

[54] ANTI-EDA MONOCLONAL ANTIBODY AND A METHOD FOR DIAGNOSIS OF DISEASE ASSOCIATED WITH THE EDA REGION OF FIBRONECTIN

[75] Inventors: Kiyotoshi Sekiguchi, Sakai; Kaneji Asakawa, Tokushima; Eiji Sakashita, Tokushima; Kazuo Hino, Tokushima; Sadahito Shin, Tokushima; Tetsuya Tachikawa, Tokushima; Hisanobu Hirano, Naruto, all of Japan

[73] Assignee: Otsuka Pharmaceutical Factory, Inc., Tokushima, Japan

[21] Appl. No.: 119,231

[22] Filed: Sep. 22, 1993

[30] Foreign Application Priority Data

Mar. 26, 1991 [JP] Japan .................................. 3-061524
Jun. 28, 1991 [JP] Japan .................................. 3-157966
Oct. 31, 1991 [JP] Japan .................................. 3-286668

[51] Int. Cl.$^6$ ........................... G01N 33/53; C12N 5/20; C07K 16/18
[52] U.S. Cl. .................. 435/71; 435/240.27; 530/388.25
[58] Field of Search ................. 530/388.25; 435/240.27, 435/172.2, 70.21, 7.1

[56] References Cited

FOREIGN PATENT DOCUMENTS 2115767  4/1990  Japan .

OTHER PUBLICATIONS

Carmonella et al., FEBS Letters 215(2):269–73, 1987.
Sekiguchi et al., Biochemistry 28:3293–3298, 1989.
Balza et al. FEBS Lett 228:42–44, 1988.
Vartio et al. Int. J. Biochem 21:307–311 1989.
Burton–Wurster et al. Arch Biochem Biophys 269:32–45 1989.
Peters et al. J. Lab. Clin. Med. 113(5):586–597, 1989.
Peters et al. Am Rev Respir Dis. 138:167–174, 1988.
Sevier et al. Clin Chem 27:1797–1806, 1981.
Novick et al. Hybridoma 8:561–7 1989.
Heyningen et al. J. Immunol. Mtds 62:147–53 1983.
Clark et al. in "Enzyme Immunoassay", Maggio, E., Ed. pp. 167–179, 1989.

*Primary Examiner*—Paula K. Hutzell
*Attorney, Agent, or Firm*—Sughrue, Mion, Zinn, Macpeak & Seas

[57] ABSTRACT

The invention provides an anti-EDA monoclonal antibody which recognizes an amino acid sequence portion in the EDA region of fibronectin (FN). The antibody of the invention has specific reactivity against EDA, in particular EDA-FN. By utilizing it, a simple and easy, high-sensitivity and high-precision immunoassay method for EDA-FN as well as a screening or diagnostic technique for EDA-FN-associated inflammatory and other diseases can be established.

5 Claims, 4 Drawing Sheets

ANTI-EDA MONOCLONAL ANTIBODY AND A METHOD FOR DIAGNOSIS OF DISEASE ASSOCIATED WITH THE EDA REGION OF FIBRONECTIN

TECHNICAL FIELD

The present invention relates to an anti-EDA monoclonal antibody and, more particularly to a novel monoclonal antibody against fibronectin (FN), in particular against FN of the type appearing in inflammatory diseases accompanied by vasculitis.

BACKGROUND ART

Fibronectin (FN) was first reported by Morrison et al. [Morrison, P. R. et al., J. Am. Chem. Soc., 70, 3103 (1948)] as one of plasma proteins in 1948. Being a group of multifunctional proteins broadly distributed in various tissues and body fluids, this substance is known to be involved, as a cell adhesion factor, in a large variety of biological events such as the migration, differentiation, proliferation and canceration of cells [Sekiguchi, K.: Cell Engineering, 4, 485–497 (1985)].

Meanwhile, FN synthesized in the liver and existing in the blood is known as plasma FN (pFN), and FN detected on the cultured cell surface and culture supernatant is called cellular FN (cFN) [Sekiguchi et al., J. Biol. Chem., 260 (8), 5105–5114 (1985)]. It has been shown that these species of FN are subject to molecular diversity due to alternative splicing of the early gene transcription product. As the regions subject to such alternative splicing, there are three regions called EDA, EDB and IIICS, and it is believed that a large number of molecular species occur according to varied combinations of expression of these regions. In pFN, the above-mentioned EDA and EDB regions have not been appreciably expressed.

On the other hand, cFN is an FN in which the level of expression of the EDA region mentioned above ([cf. Kornblihtt, A. R., et al., Nucleic Acids Res., 12, 5853–5868 (1984); Mosher, D. F. (ed.), Fibronectin, pp. 2–9, Academic Press, 1989]; while this region is referred to as "ED" in the former reference and as "EDa" in the latter reference, said region is referred to as "EDA" in the present specification) is high. Hereinafter such FN in which this EDA region has been expressed is referred as "EDA-FN" for short. Peters J. H. et al. conjugated a nonacosapeptide with keyhole limpet hemocyanin (KLH) to prepare an immunogen, constructed an anti-EDA-FN polyclonal antibody, and using the antibody, demonstrated that the blood EDA-FN level is markedly elevated in patients with collagen disease accompanied by vasculitis [Am. Rev. Respir. Dis., 38, 167–174 (1988); J. Lab. Clin. Med., 113 (5), 586–597 (1989)]. However, such a polyclonal antibody as mentioned above can be supplied only in limited amounts and may be contaminated with another antibody differing in specificity. In addition, its antibody titer varies from animal individual to animal individual.

It is reported that pFN varies in kidney diseases and thrombosis [Usui, N. and Ehara, E., Japan. J. Clin. Med., 47, Supplement, 1989, pp. 148–151]. As for the significance of this, however, many points remain unclear. No diagnostic technique has been established as yet based on the assay of pFN. No finding has been obtained with regard to EDA-FN.

Under these circumstances, means have been demanded in the art for promoting investigations into the above-mentioned EDA-FN on the molecular level, for enabling molecular species-specific assay (detection) or purification and, in its turn, for enabling the diagnosis of collagen disease (autoimmune disease), inflammatory diseases accompanied by vasculitis, as in kidney diseases, and thrombosis.

It is an object of the invention to provide means capable of satisfying the above demand. Thus, the present invention intends to provide a monoclonal antibody specifically recognizing EDA and therefore specifically reacting with EDA-FN, provide an EDA-associated peptide, in particular a specific peptide capable of serving as an immunogen for the production of the above-mentioned monoclonal antibody and as a tracer for assaying EDA-FN, and provide a technique capable of assaying the desired EDA-FN or EDA not only in the conventional solid system but also in a liquid system using said antibody and so on.

DISCLOSURE OF INVENTION

According to the invention, there is provided an anti-EDA monoclonal antibody characterized in that it recognizes an amino acid sequence portion in the EDA region of FN.

In accordance with the invention, a peptide is also provided which is a fused protein derived from protein A and a peptide having the above-mentioned amino acid sequence of the EDA region of FN.

The abbreviations used in the present specification for amino acids, peptides, protective groups, activating groups and so forth are IUPAC abbreviations or those symbols or abbreviations that are conventionally used in the relevant field of art. The nucleic acids in base sequences are also similarly expressed.

The above-mentioned specific anti-EDA monoclonal antibody provided by the present invention is an antibody specifically recognizing EDA and is characterized by its specifically reacting with EDA or FN having said region, namely EDA-FN.

Accordingly, the antibody of the invention can be used as a specific antibody in immunoassay of EDA or EDA-FN and a simple and easy high-sensitivity, high-precision assay method therefor can be established using said antibody. Once the assay method mentioned above has been established, screening and diagnosis of inflammatory diseases associated with EDA-FN is possible. The present invention thus also provides an immunoassay method for EDA or EDA-FN and a diagnostic technique for EDA-FN-associated autoimmune diseases, kidney diseases, thrombosis and gestosis, for instance. The diagnostic technique provided by the invention for the above-mentioned various diseases is very useful in studying and elucidating the mechanisms of onset of these diseases, and in like fundamental studies.

Furthermore, the antibody of the invention is useful in immunologically purifying the above-mentioned EDA or EDA-FN by affinity chromatography, among others.

In addition, the above-mentioned specific protein (EDA-protein A fused protein) provided by the invention is useful as an immunogen for the production of the anti-EDA monoclonal antibody of the invention and can also be used as a tracer or the like in the above-mentioned assay method.

A method of producing the antibody of the invention is detailedly described in the following. The antibody of the invention can be produced by a general procedure [Hanfland, P., Chem. Phys. Lipids, 15, 105–124 (1975); Hanfland, P. and Egge, H., Chem. Phys. Lipids, 16, 201–214 (1976); Koscielak, J., et al., Eur. J. Biochem., 37, 214 (1973)] using, as an immunogen, a fused protein derived from a peptide having the amino acid sequence of the above-mentioned EDA region and protein A.

The EDA region mentioned above is known and the gene therefor has been determined [Kornblihtt, A. R., et al., Nucleic Acids Res., 2, 5853–5863 (1984)].

More specifically, the above-mentioned method is carried out, for example, by preparing fused cells (hybridomas) from plasmocytes (immunocytes) of a mammal immunized with the above-mentioned immunogen and mammalian plasmacytoma cells, selecting, from among these, a clone producing the desired antibody (monoclonal antibody) capable of recognizing the EDA region of FN, and culturing said clone.

The antibody of the invention may be in the form of a crude antibody solution obtained in the above manner, namely the culture supernatant of an antibody-producing hybridoma or mouse ascitic fluid as such, or may be a purified product obtained by purifying such crude product by fractionation with ammonium sulfate or by ion exchange chromatography or using a protein A antigen column.

The above-mentioned fused protein from a peptide having the amino acid sequence of the EDA region of FN and protein A, which is used as an immunogen in the production of the antibody of the invention, is not limited to any specific one provided that it has at least the amino acid sequence of the EDA region. Thus, for example, it may be a fused protein derived from protein A and any of EDA-FN prepared from cancer cells, EDA-FN produced by the recombinant DNA technology, the EDA region of such EDA-FN or a fragment thereof, and a synthetic peptide having the above-mentioned specific amino acid sequence. Among these, the one obtained by using, as a hapten, a peptide of the amino acid sequence of the EDA region is preferred.

The above-mentioned fused protein from a peptide having the amino acid sequence of the EDA region and protein A can preferably be produced by recombinant DNA techniques using an established EDA-FN-producing cell line. The details are, for instance, as follows.

First, cDNA coding for the EDA region is synthesized using a cDNA library prepared from poly-A+ RNA of an established cell line capable of producing EDA region-containing FN, typically the normal diploid fibroblast IMR-90 isolated from a human fetal lung tissue, and following the polymerase chain reaction (hereinafter referred to as "PCR" for short; Saiki, R. K., et al., Science, 230, 1350–1354 (1985)) in accordance with the method of Kawasaki and Wang [Kawasaki and Wang, PCR Technology, H. A. Erlich, ed., Stockton Press, New York, pp. 89–98 (1989)].

Thus, using the two oligonucleotide primers shown below as an upstream primer (EcoRI site) and a downstream primer (SacI site), respectively, the PCR is carried out to amplify the EcoRI-SacI region coding for the EDA region on the FN cDNA.

Upstream primer (EcoRI site):

TCTCGGAATT CCATCACCCT CACC (SEQ. ID. NO. 1)

Downstream primer (SacI site):

GGGGAGCTCC GAGCATTGTC ATTC (SEQ. ID. NO. 2)

The two primers to be used here are not limited to the above particular base sequences but may be any ones containing the desired EcoRI or SacI site. The double-stranded cDNA obtained as mentioned above is cleaved with EcoRI and then inserted into the protein A gene fusion vector pRIT2T [Pharmacia] at the EcoRI-SmaI site, whereby the desired protein A-EDA fused protein expression vector pEDA1 can be obtained.

The transformation of a host with the above-mentioned expression vector can be carried out, for example, by the calcium phosphate method [D. Hanahan, D. M. Glover, ed., DNA Cloning, vol. 1, pp. 109–135, IRL Press, Oxford, 1985] using, as host cells, Escherichia coli N4830 [obtained from Pharmacia], which has a $\lambda CI_{857}$ temperature-sensitive repressor. The thus-obtained transformants are cultured on LB medium and then subjected to cloning referring to the method of Hanahan and Meselson [Hanahan, D. and Meselson, M., Gene, 10, 63–67 (1980)], whereby the desired protein A-EDA fused protein-positive clone can be obtained.

The desired fused protein can be produced by isolating the above-mentioned positive clone, cultivating the same, and subjecting the same to heat induction. The protein produced can be recovered by causing it to be released from cells by sonication and can be purified by chromatography using an immunoglobulin-insolubilized column. In this way, the desired purified immunogen can be obtained.

In the procedure mentioned above, the EDA gene is amplified by the PCR technique using said gene in the form of an EcoRI-SacI fragment coding for the EDA region. This is not always necessary. Thus, for instance, a restriction site upstream of the SacI site, for example the BglII site, may be used as the downstream primer. Furthermore, the gene mentioned above can also be totally synthesized by chemical nucleic acid synthesis following such a conventional method as the phosphite triester method [Nature, 310, 105 (1984)].

The mammal to be immunized with the immunogen (i.e. the protein A-EDA region peptide fused protein mentioned above) is not limited specifically. However, it is desirable to select a suitable animal in view of the amenability to the fusion of its cells with the plasmacytoma cell to be used. Generally, mice and rats are advantageously usable. The mammal is immunized by a usual method, for example, by administering the above-mentioned immunogen or an immunogen prepared by coupling a carrier (highly antigenic heterologous protein) with the fused protein mentioned above using an appropriate coupling reagent as mentioned later herein to the mammal by intravenous, intradermal, subcutaneous or intraperitoneal injection, for instance.

The carrier to be used in the production of the above-mentioned immunogen by coupling the carrier with the fused protein can be selected from among those widely diverse natural or synthetic macromolecular proteins that are conventionally used in the preparation of antigens. As examples of said carrier, there may be mentioned animal serum albumins such as horse serum albumin, bovine serum albumin, rabbit serum albumin, human serum albumin, sheep serum albumin, etc.; animal serum globulins such as horse serum globulin, bovine serum globulin, rabbit serum globulin, human serum globulin, sheep serum globulin, etc.; animal thyroglobulins such as horse thyroglobulin, bovine thyroglobulin, rabbit thyroglobulin, human thyroglobulin, sheep thyroglobulin, etc.; animal hemoglobins such as horse hemoglobin, bovine hemoglobin, rabbit hemoglobin, human hemoglobin, sheep hemoglobin, etc.; animal hemocyanins such as keyhole limpet hemocyanin (KLH) etc.; proteins extracted from ascarides (Ascaris extracts, as described in Japanese Unexamined Patent Publication No. SHO 56-16414, J. Immunol., 111, 260–268 (1973), J. Immunol., 122, 302–308 (1979), J. Immunol., 98, 893–900 (1967) and Am. J. Physiol., 199, 575–578 (1960), or further purified versions thereof); polylysine, polyglutamic acid, lysine-glutamic acid copolymer, lysine- or ornithine-containing copolymers; and the like.

As the hapten-carrier coupling reagent, use can be made of a wide variety of coupling agents conventionally used in preparing antigens. Specifically, mention may be made of diazonium compounds such as bisdiazotized benzidine (BDB), bisdiazotized 3,3'-dianisidine (BDD), etc., for crosslinking of tyrosine, histidine or tryptophan; aliphatic dialdehydes such as glyoxal, malondialdehyde, glutaraldehyde, succinaldehyde, adipoaldehyde, etc., for amino-amino crosslinking; dimaleimide compounds such as N,N'-o-phenylenedimaleimide, N,N'-m-phenylenedimaleimide, etc., for thiol—thiol crosslinking; maleimidecarboxyl-N-hydroxysuccinimide esters such as metamaleimidobenzoyl-N-hydroxysuccinimide ester, 4-(maleimidomethyl)-cyclohexane-1-carboxyl-N'-hydroxysuccinimide ester, N-succinimidyl-3-(2-pyridyldicyclo)propionate (SPDP), etc., for amino-thiol crosslinking; peptide bond formation reaction reagents generally used for amide bonding of an amino group and a carboxyl group, for example dehydrating condensing agents such as carbodiimides, e.g. N,N'-dicyclohexylcarbodiimide (DCC), N-ethyl-N'-dimethylaminocarbodiimide, 1-ethyl-3-diisopropylaminocarbodiimide, 1-cyclohexyl-3-(2-morpholinyl-4-ethyl)carbodiimide, etc. Also usable as the hapten-carrier coupling reagent mentioned above are combinations of a diazoniumarylcarboxylic acid, such as p-diazoniumphenylacetic acid, and a conventional peptide bond formation reaction reagent, such as one of the dehydrating condensing agents mentioned above.

The reaction for immunogen production using the above-mentioned hapten, carrier protein, hapten-carrier coupling reagent, spacer and so forth can be carried out in the conventional manner, generally in an aqueous solution or an ordinary buffer solution with a pH of about 5 to 10, preferably about 6 to 9, at 0° to 40° C., preferably around room temperature. Said reaction is generally complete in about 2 to 5 hours.

In the above reaction, the proportions of the hapten, hapten-carrier coupling reagent and carrier can suitably be selected and, generally and advisably, the carrier is used in a proportion of about 0.5 to 5 parts by weight, preferably about 1 to 2 parts by weight, per part by weight of the hapten, and the hapten-carrier coupling reagent in a proportion of about 1 to 30 moles per mole of the hapten. In the above manner, the desired immunogen, which is a hapten-carrier conjugate formed by coupling of the carrier to the hapten either directly or by the intermediary of a spacer, can be obtained. After completion of the reaction, the antigen obtained can be readily purified in the conventional manner, for example by dialysis, gel filtration, fractional precipitation, etc.

The immunization mentioned above can be realized, more specifically, by diluting the immunogen to an appropriate concentration with phosphate-buffered physiological saline (PBS) or physiological saline, for instance, and administering the dilution to test animals several times at 2- to 14-day intervals, where appropriate combinedly with an ordinary adjuvant, at a total dose of about 10 to 100 μg per mouse, or about 0.2 to 2.0 mg per rabbit, for instance. Usable as the adjuvant mentioned above are pertussis vaccine, complete Freund's adjuvant, alum, etc.

After the lapse of 1 to 2 weeks following the last immunogen administration mentioned above, the antibody is collected by taking blood from the immunized animals, centrifuging the blood and isolating the serum.

As the immunocytes to be used in the monoclonal antibody production mentioned above, splenocytes collected about 3 days after the last administration mentioned above are preferred. Available as mammalian plasmacytoma cells as the other host cells to be fused with the immunocytes are various known cell lines including myeloma cells, such as P3-X63-Ag8 (X63) [Nature, 256, 495–497 (1975)], P3-X63Ag8-U1 (P3-U1) [Current Topics in Microbiology and Immunology, 81, 1–7 (1978)], P3-NSI-1-Ag4-1 (NS-1) (Eur. J. Immunol., 6, 511 –519 (1976)], Sp2/0-Ag14 (Sp2/0 [Nature, 276, 269–270 (1978)], FO [J. Immunol. Meth., 35, 1–21 (1980)], etc., and rat 210RCY3-Ag1.2.3 (Y3) [Nature, 277, 131 (1979)].

The fusion between the immunocytes and plasmacytoma cells is conducted basically by a known method, such as the method of Milstein et al [Methods in Enzymology, Vol. 73, p. 3 (1981)]. More specifically, the fusion reaction is conducted, for example, in a usual nutrient medium in the presence of a usual fusion promoting agent such as polyethylene glycol (PEG) or Sendai virus (hemagglutinating virus of Japan, HVJ). To achieve an improved fusion efficiency, auxiliary agents such as dimethyl sulfoxide can be added to the medium when necessary. The electric treatment (electrofusion) method may also be used where appropriate. The immunocytes and plasmacytoma cells are used in a usual ratio. For example, immunocytes are used in a proportion of about 1 to about 10 times the number of plasmacytoma cells. Examples of the medium useful for the fusion are RPMI-1640 medium and MEM medium which are usually used for proliferating plasmacytoma cells, and various other media which are used for cultivating cells of this type. Generally it is desirable to use such media with the serum supplement, such as fetal calf serum (FCS), removed therefrom.

To effect cell fusion, predetermined quantities of immunocytes and plasmacytoma cells are thoroughly mixed together in the medium, and a solution of PEG having an average molecular weight of about 1000 to about 6000 is admixed, as preheated to about 37° C., with the medium usually at a concentration of about 30 to about 60 w/v %. Subsequently, a suitable medium is admixed with the culture from time to time, each time followed by centrifugation and removal of the supernatant. Repetition of this procedure gives the desired hybridoma.

The desired hybridoma obtained is separated by incubation in a usual selection medium such as HAT medium (containing hypoxanthine, aminopterin and thymidine). The incubation with the HAT medium is conducted for a period of time usually several days to several weeks, which is sufficient to extinguish the cells (e.g. unfused cells) other than the desired hybridoma cells. The hybridoma cells obtained are then subjected to the usual limiting dilution method to retrieve the clones producing the desired antibody, followed by the production of monoclonal antibody.

The desired antibody-producing clones can be sorted out by various methods which are generally used for detecting antibodies ["Hybridoma Method and Monoclonal Antibodies," published by R & D Planning Co., Ltd., pp. 30–53, Mar. 5, 1982], such as the ELISA method [Engvall, E., Meth. Enzymol., 70, 419–439 (1980)], plaque method, spot method, agglutination method, Ouchterlony method and radioimmunoassay (RIA). The immunizing antigen mentioned above is usable for this sorting out procedure.

The hybridoma thus obtained and producing the desired monoclonal antibody of the invention can be subcultured in a usual medium and preserved for a prolonged period of time in liquid nitrogen.

The monoclonal antibody of the invention can be collected from the antibody-producing hybridoma as a culture supernatant by cultivating the hybridoma in the usual manner, or as the ascites of a mammal which is amenable to the proliferation of the hybridoma, by administering the hybridoma to the animal. The former method is suitable for preparing the antibody with a high purity, while the latter method is suited to large quantity production of the antibody. The above-obtained antibody can be further purified by a usual method such as salting out, gel filtration, affinity chromatography or the like. In this way, the anti-EDA monoclonal antibody of the invention can be produced.

The applications of the antibody of the invention are detailedly described in the following. Using said antibody, the EDA region of FN can be purified in a simple and specific manner by conventional purification means such as immunoprecipitation, affinity chromatography, etc. Further, EDA-FN in a sample, for example a body fluid, can be specifically assayed in the manner of immune reaction using the antibody of the invention. For said assay, conventional immunological means can be used, for example radioimmunoassay (RIA) by the competitive or sandwich technique, enzyme immunoassay (ELISA) or the agglutination method. The operation and procedure of each method may be those known in the art.

More specifically, when, for instance, the competitive method is employed, the EDA-FN to be assayed in a sample is allowed to react with a given amount of the antibody of the invention, labeled with a label, in competition with the EDA of a given amount of insolubilized FN, then the complex of the EDA of the insolubilized FN and the labeled antibody is separated from the unconjugated labeled antibody, and the activity of the label of one of them is determined, whereby the EDA-FN in the sample can be assayed. In carrying out the sandwich method, the material to be tested (sample) is allowed to react with the antibody of the invention in insolubilized form, the thus-formed FN EDA-insolubilized antibody complex is then reacted with a given amount of a labeled antibody, and the activity of the label on the sandwich formed from said complex and labeled antibody or the unbound label activity is measured, whereby the EDA-FN in the sample can be assayed in the same manner as mentioned above.

In the above-mentioned various assay methods, the sample may be a body fluid, such as blood, urine, a cell or tissue fluid, or the like. Among them, blood samples, in particular, serum and plasma samples are preferred.

The antibody of the invention as labeled with a label as well as the labeled antibody can be prepared in the conventional manner using an appropriate label. The label may be any of the conventional ones, for example radioactive substances such as $^{125}I$, $131'$, tritium, etc., and various enzyme reagents such as glucoamylase, peroxidase (POX), chymotrypsinogen, procarboxypeptidase, glyceraldehyde-3-phosphate dehydrogenase, amylase, phosphorylase, alkaline phosphatase, DNase, PNase, $\beta$-galactosidase, glucose-6-phosphate dehydrogenase, ornithine decarboxylase, etc. In the case of radioactive iodine, the labeling is carried out by oxidative iodization using choloramine T [W. M. Hunter and F. C. Greenwood, Nature, 194, 495 (1962); Biochem. J., 89, 144 (1963)], for instance. Enzyme reagent introduction can be effected by the usual coupling method, for example by the method of Erlanger et al. [B. F. Erlanger et al., Acta Endocrinol. Suppl.,168, 206 (1972)] or the method of Karol et al. [M. H. Karol et al., Proc. Natl. Acad. Sci. U.S.A., 57, 713 (1967)].

The insolubilized antibody of the invention and the insolubilized FN EDA, for instance physically or chemically immobilized on a plate, can be prepared by chemically or physically binding the antibody of the invention or EDA to an appropriate insoluble carrier. As example of the carrier that can be used, there may be mentioned powdered cellulose, Sephadex, Sepharose, polystyrene, filter paper, carboxymethylcellulose, ion exchange resins, dextran, plastic films, plastic tubes, nylon, glass beads, silk, polyamine-ethyl vinyl ether-maleic acid copolymers, amino acid copolymers, ethylene-maleic acid copolymers, etc. The insolubilization can be effected by using various chemical reaction means, for example covalent binding methods such as the diazo method, peptide method and alkylation method, the carrier coupling method using a crosslinking reagent (using, as the crosslinking reagent, glutaraldehyde, hexamethylene isocyanate or the like) and the carrier coupling method utilizing the UgI reaction, ionic binding methods using such a carrier as an ion exchange resin, physical adsorption methods using a porous glass, for example glass beads, as the carrier, and so on.

Generally, the reaction (immune reaction) in the above assay methods can be effected at a temperature of not higher than 45° C., preferably 4° to 40° C., and requires about several to 24 hours.

Thus, when the antibody of the invention is used, EDA-FN or FN possessing EDA in samples can be assayed in a simple and easy manner and with high precision.

Establishment of purification systems and assay systems using the antibody of the invention as well as modifications and applications of such systems is obvious to those having ordinary skill in the art.

EFFECTS OF THE INVENTION

The present invention provides an anti-FN EDA monoclonal antibody and an FN EDA-protein A fused protein capable of serving as an immunogen in the production of said monoclonal antibody. The invention further provides an assay technique for EDA-FN in which the above-mentioned antibody of the invention is used, and also a method of diagnosing and/or treating inflammatory diseases accompanied by vasculitis, or thrombosis, gestational toxicosis, and like various diseases.

BEST MODES FOR CARRYING OUT THE INVENTION

The following examples illustrate the present invention in further detail. It is to be noted, however, they are by no means limitative of the scope of the present invention.

EXAMPLE 1

Production of an EDA-protein A Fused Protein (1)
Preparation of an EcoRI-SacI cDNA Fragment
Including the EDA Region of FN a) Amplification of the Human Fibroblast cDNA Library Using the cDNA library (Clonetek) prepared from the poly $A^+$ RNA of human fibroblast cell line IMR-90 using lambda phage $\lambda$gt11 as the vector, amplification of the phage was carried out by the plate lytic growth method. Thus, 1 µl of a phage suspension from the above cDNA library was diluted with 99 µl of SM medium [1M NaCl, 20 mM $MgSO_4.7H_2O$, 50 mm Tris-HCl and 0.1% gelatin] and mixed with 100 µl of an overnight culture of E. coli LE392 in LB medium [1% Bacto trypton, 0.5% Bacto yeast extract and 0.5% sodium chloride] and the mixture was incubated at 37° C. for 10 minutes, whereby the phage was adsorbed on the E. coli. To this was added 7.5 ml of a top agar solution [0.7% Bacto agar in LB medium] kept warm at about 50° C. and the mixture was overlayered on LB agar [LB medium containing 1.5% of Bacto agar] in a Petri dish 15 cm in diameter. After solidification of the top agar, culture was carried out at 37° C. overnight for phage amplification. Then, 15 ml of SM medium was poured onto the top agar and the dish was incubated at 4° C. for 1 hour. The phage was recovered together with the top agar and centrifuged at 18000 rpm (Hitachi refrigerated centrifuge, RPR 20-2 S rotors) for 10 minutes to remove the top agar and E. coli. To the phage-containing supernatant were added NaCl and polyethylene glycol at the final concentrations of 1M and 10% respectively, and the mixture was allowed to stand on ice for 1 hour. The mixture was centrifuged again at 18000 rpm for 10 minutes to recover the phage as a pellet. This pellet was dissolved in 2 ml of 20 mM Tris-HCl (pH 7.5)-10 mM MgSO$_4$ followed by addition of 20 µl of DNase I (10 mg/ml). The mixture was allowed to stand at room temperature for 30 minutes to lyze the free DNA and the same volume of chloroform was added and the whole was stirred for 5 minutes and centrifuged at 3000 rpm for 10 minutes to separate the water layer from the chloroform layer. The water layer was recovered and stirred well with the same volume of phenol to remove the coat protein from the phage particles, after which it was centrifuged at 3000 rpm for 10 minutes to transfer the phage DNA to the water layer. The water layer was extracted with the same volume of chloroform again and 0.2 volume of 3 M sodium acetate solution and 2 volumes of ethanol were added to the water layer. The mixture was allowed to stand at −80° C. for 10 minutes and, then, centrifuged at 15000 rpm for 10 minutes to recover the phage DNA as a pellet. The DNA thus obtained was dissolved in TE buffer [10 mM Tris-HCl (pH 7.4)-1 mM EDTA] at a final concentration of 0.5 µg/µl and preserved at −20° C. The purity of phage DNA was verified by 1% agarose gel electrophoresis. b) Synthesis of Primers The following two oligodeoxynucleotide primers were prepared.
Upstream primer (EcoRI site)

TCTCGGAATT CCATCACCCT CACC (SEQ ID NO. 1)
Downstream primer (SacI site)

GGGGAGCTCC GAGCATTGTC ATTC (SEQ ID NO. 2)

The above primers were synthesized from β-cyanoethylphosphoamidite derivatives of 4 different bases by the solid-phase method using an automatic DNA synthesizer (Applied Biosystems 380A). The deprotection and detachment from the solid phase of the synthesized oligodeoxynucleotides were carried out by warming in concentrated aqueous ammonia at 55° C. for 10 hours. The synthetic oligonucleotides thus prepared were purified by HPLC to give about 50 µg each of the desired oligonucleotides for use as the upstream and downstream primers. The resulting purified oligonucleotides were dissolved in TE buffer and preserved at −20° C.
c) Amplification of the EcoRI-SacI cDNA Fragment A 1 µl portion of the TE buffer containing 0.5 µg of DNA as prepared in a) above was diluted with 1×PCR reaction buffer [20 mM Tris-HCl, pH 8.4; 50 mM KCl; 2.5 mM MgCl$_2$; 0.1 mg/ml nuclease-free bovine serum albumin] containing 20 pmol each of the upstream and downstream primers, followed by addition of 5 U of Taq polymerase (Perkin Elmer-Cetus, 1 µl ). After 100 µl of mineral oil was overlayered, the mixture was subjected to 30 heating cycles of 1.5 minutes at 95° C., 3 minutes at 50° C. and a further 3 minutes at 72° C. to amplify the EcoRI-SacI cDNA fragment coding for the desired EDA region. The above reaction mixture was subjected to 1% agarose gel electrophoresis using the HaeIII-cut DNA fragments of øx174 DNA as molecular weight markers in the presence of ethidium bromide to confirm that the object EcoRI-SacI cDNA fragment having the size of 1400 base pairs had been amplified.

d) Purification of the EcoRI-SacI cDNA Fragment

The EcoRI-SacI fragment isolated on the agarose gell in c) above was adsorbed on a DEAE-cellulose membrane (S & S, NA 45) by the method of Dretzen, G. M. et al. [Anal. Biochem., 112, 295–298 (1981)] and the adsorbed DNA fragment was then eluted from the DEAE-cellulose membrane with an eluent buffer [50 mM Tris-HCl, pH 8.0; 1M NaCl; 10 mM EDTA] and precipitated with cold ethanol to recover the object EcoRI-SacI fragment (about 100 ng).

(2) Insertion of the EcoRI-SacI cDNA including the EDA Region Into The Protein A Expression Vector pRIT2T
a) Preparation of the Plasmid Vector Two µg of protein A gene-fused vector pRIT2T (Pharmacia) was dissolved in 20 µl of EcoRI-SmaI reaction buffer [33 mM Tris-acetate, pH 7.9; 10 mM magnesium acetate; 66 mM potassium acetate; 0.5 mM dithiothreitol; 0.01% bovine serum albumin] followed by addition of 10 units each of EcoRI and SmaI. The mixture was incubated at 37° C. for 2 hours to cleave the plasmid DNA at EcoRI-SmaI sites. The reaction mixture was extracted with phenol and the cleaved DNA (about 1 µg) was recovered by ethanol precipitation.
b) Insertion of the PCR-amplified EcoRI-SacI cDNA Fragment Into the Plasmid Vector In 20 µl of EcoRI reaction buffer [50 mM Tris-HCl, pH7.5; 10 mM MgCl$_2$; 1 mM dithiothreitol; 100 mM NaCl] was dissolved 100 ng of the EcoRI-SacI cDNA fragment purified in (1)-d) above, followed by addition of 5 U of EcoRI, and the mixture was incubated at 37° C. for 3 hours to expose the 5' end EcoRI site of the amplified EcoRI-SacI fragment. The reaction mixture was then extracted with phenol and after addition of 20 ng of the pRIT2T plasmid cleaved at the EcoRI-SmaI site which was prepared in (2)-a), cold ethanol precipitation was carried out to recover the DNA. This DNA was dissolved in 24 µl of ligation buffer [66 mM Tris-HCl, pH 7.6; 5 mM MgCl$_2$; 5 mM dithiothreitol; 1 mM ATP] followed by addition of 300 U of T4 DNA ligase (Takara Shuzo), and the mixture was incubated at 16° C. for 16 hours to insert the EcoRI-Sac I cDNA fragment encoding the EDA region of FN in the EcoRI-SmaI site of pRIT2T.
c) Construction of the Transformant A 1 µl portion of the reaction mixture obtained in b) above was mixed with 100 µl of E. coli HB101 competent cells (Takara Shuzo) and the mixture was maintained under ice-cooling for 30 minutes and incubated at 42° C. for 90 seconds to introduce the plasmid DNA into the E. coli.

To this mixture was added 1 ml of LB medium and shake culture was carried out at 37° C. for 1 hour. Then, 100 µl of the culture was inoculated on LB agar medium containing 50 µg/ml of ampicillin and the inoculated agar was incubated at 37° C. for 14 hours to obtain about 50 colonies of E. coli transfected by the plasmid DNA. From among them, 12 colonies were randomly harvested and cultured in LB medium containing 50 µg/ml of ampicillin. Then, in accordance with the method of Birnboim and Doly as modified [Molecular Cloning, A Laboratory Manual, T. Maniatis et al., edit., 368–369 (1982)], the plasmid DNA was recovered from each colony. This DNA was double-digested with EcoRI and BamHI and a plasmid clone (pEDA1) having the predicted insert sequence of about 1400 base pairs was selected.

(3) Expression and Isolation of the Protein A-EDA Fused Potein
a) Introduction of Plasmid pEDA1 Into E. coli N4830

The pEDA1 plasmid DNA obtained in (2) above was introduced into E. coli N4830 (obtained from Pharmacia) in accordance with the calcium phosphate method of Mandel and Higa [J. Mol. Biol., 53, 154 (1970)], as follows.

Thus, E. coli N4830 was shake-cultured in 100 ml of LB medium at 37° C. and when the cell density reached about $5 \times 10^7$/ml, the incubation was terminated and the culture was quenched in an ice bath. The quenched culture was centrifuged at 4000 33 g (4° C.) for 5 minutes to harvest the cells. The pellet was suspended in 50 ml of ice-cooled 50 mM calcium chloride-10 mM Tris-HCl (pH 8.0) and the suspension was allowed to stand in an ice bath for 15 minutes and, then, centrifuged at 4000 × g (4° C.) for 5 minutes. The resulting pellet was resuspended in 7 ml of an ice-cooled solution of 50 mM calcium chloride-10 mM Tris-HCl (pH 8.0) and the suspension was allowed to stand in an ice bath. To 0.2 ml of the E. coli cell suspension thus prepared was added 10 µl of a solution of pEDA1 in TE buffer (containing 10 in an ice bath for 30 minutes, after which it was warmed in a water bath at 42° C. for 2 minutes. After 1 ml of LB medium was added, the mixture was incubated at 37° C. for 1 hour. The E. coli cell suspension thus obtained, 100 µl, was spread on an ampicillin-containing LB agar medium and incubated at 37° C. for 14 hours to cause production of transformant E. coli colonies.

b) Isolation of the Protein A-EDA Fused Protein

The transformant obtained in a) above (E. coli N4830 transfected with plasmid pEDA 1) was shake-cultured in 500 ml of LB medium at 30° C. for 14 hours, and after 500 ml of LB medium warmed to 54° C. beforehand was added, shake culture was further continued in a water bath at 42° C. for 90 minutes to induce expression of the protein A-EDA fused protein.

The culture was centrifuged at 5000 × g (4° C.) for 15 minutes to recover the cells, which were then suspended in 100 ml of ice-cooled Tris-buffered physiological saline [50 mM Tris-HCl (pH 7.6), and 150 mM NaCl] and disrupted by sonication in an ice bath (Branson Sonifier 250; 3 cycles of 3-minute treatment at output setting 7) to thereby release the protein from the cells. About 100 ml of this fluid was centrifuged (16000 × g, 20 minutes, 4° C.) to recover about 95 ml of a supernatant fraction. This fraction was diluted with 300 ml of Tris-buffered physiological saline and applied to a column packed with about 10 ml of IgG-sepharose 6 Fast Flow (Pharmacia) for adsorption of the protein A-EDA fused protein on the column. This column was washed with 100 ml of Tris-buffered physiological saline and 20 ml of 5 mM ammonium acetate (pH 5.0) in that order and the adsorbed protein was eluted with 0.5M acetic acid solution. The protein A-EDA fused protein was dialyzed against Tris-buffered physiological saline for 48 hours to give about 1 mg of the object antigen.

EXAMPLE 2

Construction of the Hybridoma

The purified protein A-EDA fused protein obtained in Example 1 above, 0.05 mg, was diluted with 0.5 ml of PBS and emulsified with the same quantity of complete Freund's adjuvant. The resulting emulsion was administered intradermally in 0.2 ml portions to male Balb/c mice (aged 8 weeks). The animals were immunized by further 4 similar doses given at 2-week intervals and the spleen was excised 3 days after the last immunization.

Splenic cells were isolated from the excised spleen and the erythrocytes present among the cells were removed by 1–2 minute lysis with 0.83% ammonium chloride solution at 4° C. The cells thus obtained were collected as sensitized lymphocytes and washed three times with RPMI-1640 medium previously warmed to 37° C.

Then, mouse myeloma cells [P3U1, Current Topics in Microbiology and Immunology, 73, 3 (1981)] was subcultured in a medium prepared by adding 100 µM of 8-azaguanine to RPMI-1640 supplemented with 15% FCS (fetal calf serum) and the cultured cells, designated as myeloma cells, were washed.

The above myeloma cells were mixed with the sensitized lymphocytes in a cell count ratio of 1:10 in a 50 ml tube and the resulting cell mixture was centrifuged at 500 × g for 5 minutes. The supernatant was thoroughly removed with a Pasteur's pipet. The above procedure was carried out in a water bath maintained at 37° C.

Then, 4 ml of 35% polyethylene glycol 1500 (Wako Pure Chemical; PEG) was added and the mixture was stirred gently for 1 to 2 minutes and allowed to stand for 1 minute, at the end of which time 2 ml of FCS-free RPMI-1640 medium, prewarmed to 37° C., was gradually added over a period of about 1 minute. The mixture was allowed to stand for 1 minute and 4 ml of the same medium was further added. After further 2-minute standing, 4 ml of the same medium was further added and the mixture was allowed to stand for 4 minutes. Thereafter, 8 ml of RPMI-1640 containing 15% FCS, 0.05 (potency)/l of streptomycin sulfate, 60000 U/l of penicillin G potassium, 54 mg/l of gentamicin and 1 ml of pyruvate (hereinafter referred to as complete RPMI-1640 medium), warmed to 37° C. beforehand, was added over a period of 2 to 3 minutes. The mixture was then centrifuged at 500 × g for 5 minutes. The supernatant was aspirated off and the splenocytes were suspended in complete RPMI-1640 medium, prewarmed to 37° C., at a concentration of $1 \times 10^6$ cells/ml. This suspension was then distributed, 0.1 ml per well, into the wells of a 96-well plate (Costar) and cultured in an incubator controlled at 37° C., 5% $CO_2$ and 100% RH for 24 hours. Thereafter, each well was filled with 0.1 ml of 10% FCS-complete RPMI-1640 medium containing $1 \times 10^{-4}$M hypoxanthine, $4 \times 10^{-7}$M aminopterin and $1.6 \times 10^{-5}$M thymidine (hereinafter referred to as HAT medium). On the 2nd and 3rd days, 0.1 ml each of the supernatant was aspirated and 0.1 ml each of fresh HAT medium was added instead. This change of medium was further performed every 2 to 3 days. On the 6th day, the supernatant was similarly aspirated and complete RPMI-1640 medium containing $1 \times 10^{-4}$M hypoxanthine and $1.6 \times 10^{-5}$M thymidine (hereinafter referred to as HT medium) was substituted. Thereafter, growth was maintained in complete RPMI-1640 medium.

After the cell fusion by the above procedure, colonies became visible in 10 to 14 days. Starting when the cells had occupied one-quarter of the bottom surface area of the 96-well plate, the culture supernatant was tested by the enzyme-linked immunosorbent assay (ELISA) using an EDA-carrying human placental FN as the antigen and from the positive well, hybridoma cloning was immediately performed by the limiting dilution method [Methods in Enzymology 73, 3 (1981)]. Thus, using 20 ml of a 10% FCS-added RPMI-1640 medium prepared to contain $1 \times 10^8$ Balb/c mouse thymic cells, cloning was performed by seeding a 96-well plate with 0.2 ml portions of the hybridoma at the rates of 3 cells/well, 1 cell/well and 0.3 cell/well to establish the object hybridoma.

The above cloning was performed 4 times with monitoring to confirm lack of reactivity with plasma FN using, as an indicator, the reactivity with the placental FN and cellular FN purified from a culture supernatant of the WI-38VA13 cell line which had been established by infecting the human normal fibroblast cell line WI-38 with the tumor virus SV40. By the above procedure was obtained a hybridoma producing the monoclonal antibody of the present invention with the desired reaction selectivity. This hybridoma clone was designated as HHS-01.

The clone HHS-01 obtained above was cultured in complete RPMI-1640 medium under the conditions of 5% $CO_2$ and 37° C. for 96 hours. The resulting culture was centrifuged at 3,000 rpm for 10 minutes to obtain a culture supernatant containing the object monoclonal antibody.

The thus-selected clone (hybridoma HHS-01 producing the antibody of the invention) has been deposited with the Fermentation Research Institute of the Agency of Industrial Science and Technology on Feb. 28, 1991, under the designation of HHS-01, where the accession number assigned is FERM BP-3297.

The above clone HHS-01 was intraperitoneally administered in a dose of $1 \times 10^6$ to Balb/c mice which had been inoculated with pristane (Aldrich). After 10 to 14 days, the accumulated ascitic fluid was harvested to recover an ascitic fluid containing the antibody of the invention.

The antibody in the ascites was purified by affinity chromatography using protein A-Sepharose to give a purified HHS-01 antibody.

The subclass of this antibody as determined by the method of Ouchterlony [Weir, D.M., Handbook of Experimental Immunology 3rd edit., Blackwell, Oxford (1978)] using a monoclonal antibody typing kit (Bindingsite, code RK008) was $IgG_{2a}$.

The characteristics of the monoclonal antibody of the invention as obtained in Example 2 are shown below in Example 3.

EXAMPLE 3

Characteristics of the Monoclonal Antibody of the Invention

The monoclonal antibody of the invention (HHS-01 antibody) was dissolved in Dulbecco's phosphate-buffered saline (D'PBS; pH 7.2) at a concentration of 2 µg/ml and this solution was distributed into the wells of a 96-well plastic plate in portions of 100 µl/well and allowed to stand at 4° C. overnight for conversion to solid phase. The plate was then washed with D'PBS [containing 0.05% of Tween 20, 300 µl/well, once]. Then, each well was filled with 300 µl each of D'PBS, 0.05% thimerosal and 0.5% bovine serum albumin (BSA) and allowed to stand at 4° C. overnight for blocking. After blocking, the wells were washed with D'PBS [containing 0.05% of Tween 20, 300 µl/well, once] and each well was filled with 100 µl of 0.1M phosphate buffer [0.05% thimerosal, 10 mM EDTA, 20% normal goat serum and 1% normal mouse serum, pH 6.0] (buffer A). Then, each well was filled with 20 µl of one of dilutions in various concentrations of FN purified from human plasma (pFN) and cellular FN (cFN) purified from a culture supernatant of the cell line WI-38VA13, which had been obtained by infecting the human normal fibroblast cell line WI-38 with a tumor virus, and the mixture was incubated at room temperature for 2.5 hours. The wells were, then, washed 5 times with D'PBS containing 0.05% of Tween 20.

Then, each of the above wells was filled with the anti-FN monoclonal antibody [OAL-pF115; established using Sigma's pFN as an immunogen; cf. Rinsho Byori, vol. 35 supplement, 1987, p.119; The 18th Congress of the International Association of Medical Laboratory Technologists, Abstracts, p. 225 (1988); etc.] (5000-fold dilution, 100 µl/well) labeled with peroxidase (periodate method) and buffer A minus EDTA (100 µl/well), and the mixture was incubated for 2.5 hours and washed 5 times with D'PBS containing 0.05% of Tween 20.

Then, 100 µl/well of o-phenylenediamine solution (OPD solution) was added and the reaction was conducted at room temperature for 10 minutes. The reaction was terminated with 100 µl of 2N sulfuric acid and the optical density at 492 nm was measured.

The results are shown in FIG. 1.

In the figure, the ordinate indicates the optical density (OD) at 492 nm and the abscissa the concentration of FN. The results shown by (1) are those for cellular FN and the results shown by (2) are those for plasma FN.

From said figure, it is apparent that the antibody of the invention does not react with plasma FN but reacts with cellular FN in a dose-dependent manner.

EXAMPLE 4

Determination of Plasma EDA-FN Levels in Patients with Rheumatoid Arthritis

Then, using the monoclonal antibody of the invention as obtained above, the EDA-FN levels in plasma samples from patients with rheumatoid arthritis (RA) were determined and compared with those in normal subjects.

Thus, first, using EDA-containing, human placenta-derived FN, diluted at various concentrations, as a standard, optical density measurement was performed following the procedure of Example 3 and a working curve was constructed.

The results obtained are shown in FIG. 2 [ordinate; optical density (OD) at 492 nm; abscissa; concentration of FN (ng/ml)].

Then, blood was sampled from seven patients with rheumatoid arthritis and, after addition of EDTA as an anticoagulant, plasma fractions were separated and used as samples. With the plasma samples, optical density measurement was performed in the same manner as in Example 3 and EDA-FN concentrations were determined based on the working curve mentioned above. For seven normal subjects as well, EDA-FN levels in plasma were determined in the same manner.

The results are shown in FIG. 3. In the figure, measured values for the normal subjects and patients with RA are plotted, with the plasma EDA-FN concentration (ng/ml) on the ordinate.

As is apparent from FIG. 3, the use of the monoclonal antibody of the invention revealed with good precision that the plasma EDA-FN levels in patients with rheumatoid arthritis (RA patients) were much higher as compared with normal subjects. Thus, the monoclonal antibody of the invention is very useful in the diagnosis of rheumatoid arthritis accompanied by vasculitis.

EXAMPLE 5

Determination of Plasma EDA-FN Levels in Patients with Renal Failure and in Patients with Diabetes Mellitus Using the monoclonal antibody of the invention and following the procedure of Example 4, plasma EDA-FN levels were measured for 45 patients with renal failure and 63 patients with diabetes mellitus and compared with the level in normal subjects.

The measured values in 51 normal subjects gave a mean value of 351 ng/ml. On the contrary, the mean value for the 45 renal failure patients was 667 ng/ml and the mean value for the 63 diabetic patients was 529 ng/ml. Diabetic patients with a complication of kidney disease showed values as high as or higher than 900 ng/ml.

Furthermore, the 45 renal failure patients were divided into two groups: 27 patients showing tendency toward thrombosis and 18 patients showing no such tendency. The two groups were compared with respect to the proportion of EDA-FN to the total FN. For total FN determination, Funakoshi' Human Fibronectin EIA Kit (Cat. No. BT-500) was used.

The mean value for the 51 normal subjects was 0,135%, the mean value for the 27 renal failure patients showing tendency toward thrombosis was 0.485% and the mean value for the 18 renal failure patients without such tendency was 0.198%.

The antibody of the invention thus proved to be useful also in the prediction of the risk of progression of diabetes mellitus or the like to kidney disease, in particular to renal failure or in the prediction of the risk of thrombosis.

The results are shown in FIG. 4. The plasma EDA-FN level for the normal pregnant women was 298±11 ng/ml (mean±SD) while the patients with gestational toxicosis gave a significantly higher value of 1137±665 ng/ml (mean±SD). From this fact, it is apparent that the monoclonal antibody of the invention can be efficiently utilized in the predictive diagnosis of gestational toxicosis.

Figure 1:
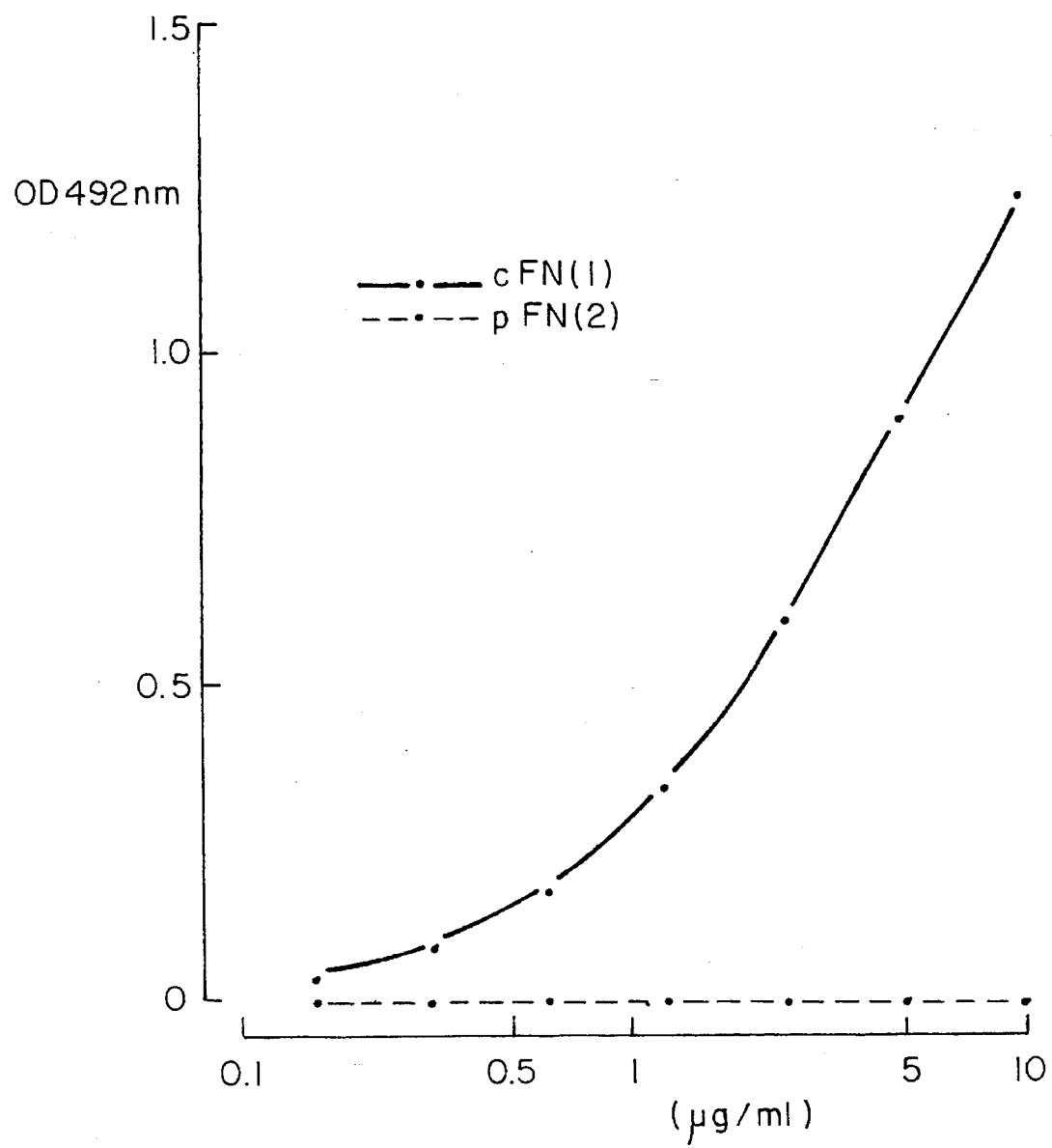
FIG. 1 is a graphic representation of the results of a reactivity study of the antibody of the invention against different FN species as performed in accordance with Example 3.
Figure 2:
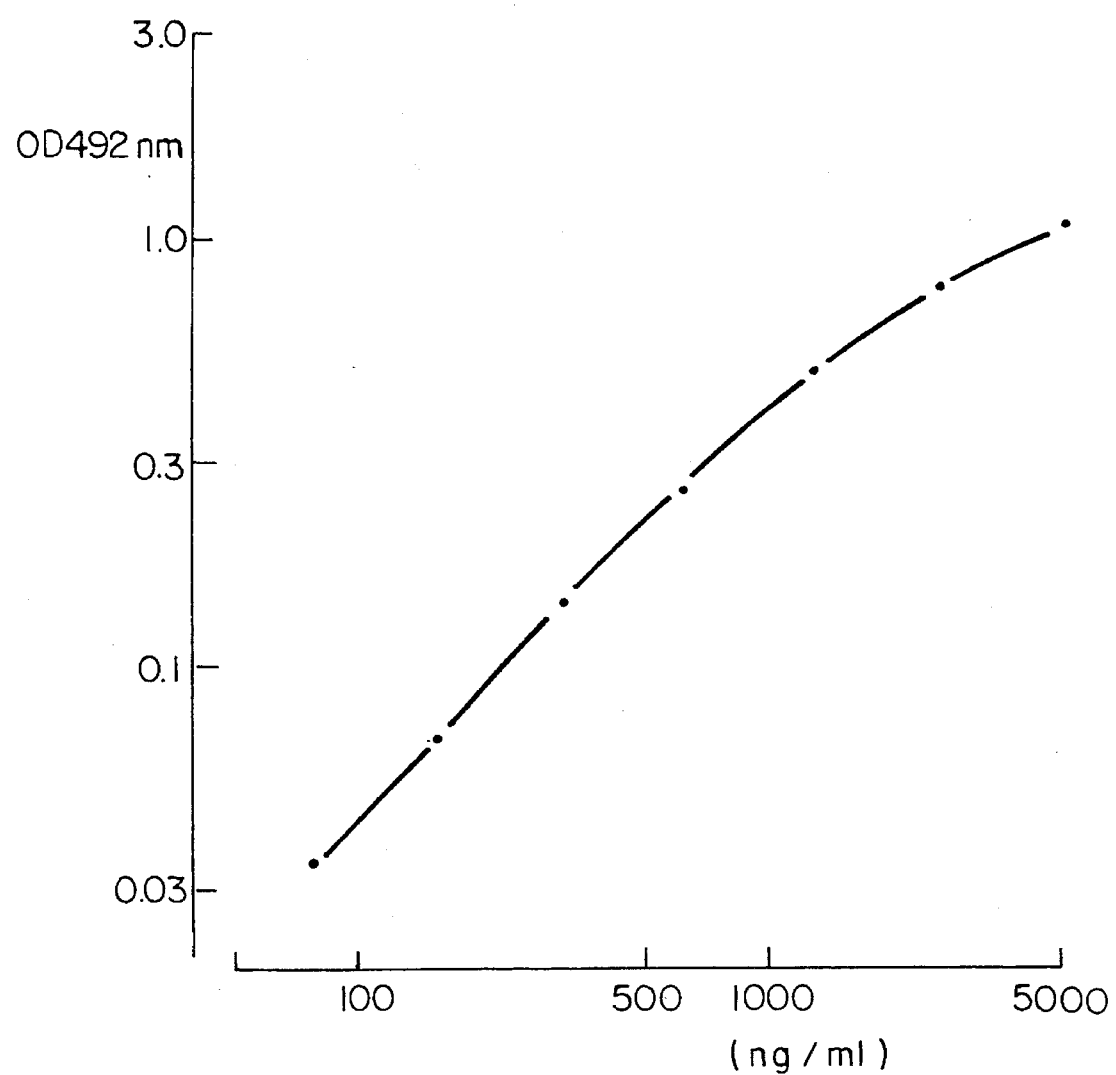
FIG. 2 is a working curve for EDA-containing, human placenta-derived FN as constructed in accordance with Example 4.
Figure 3:
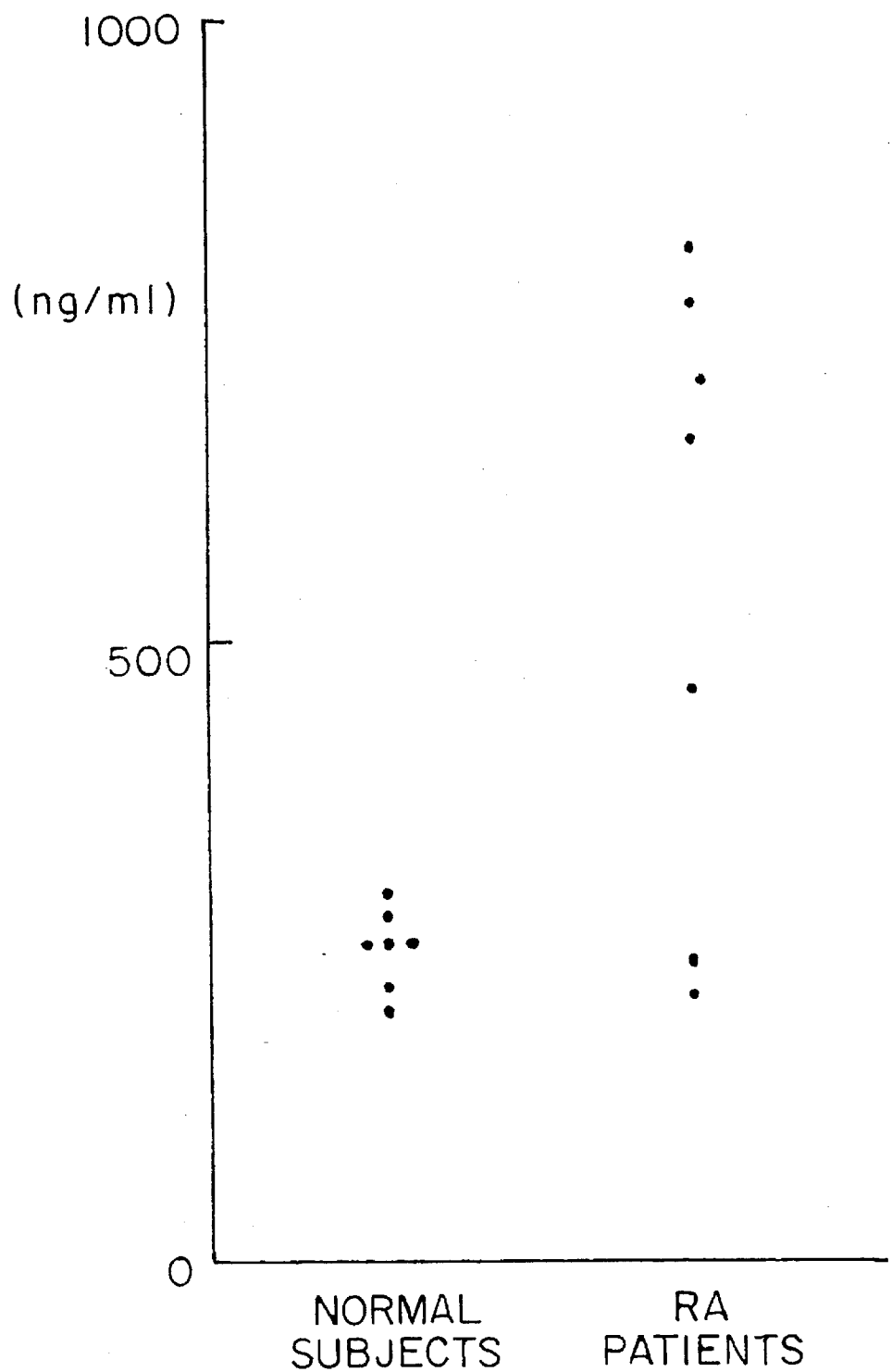
FIG. 3 is a graphic representation of the plasma EDA-FN levels in normal subjects and RA patients as determined in accordance with Example 4, as plotted.
Figure 4:
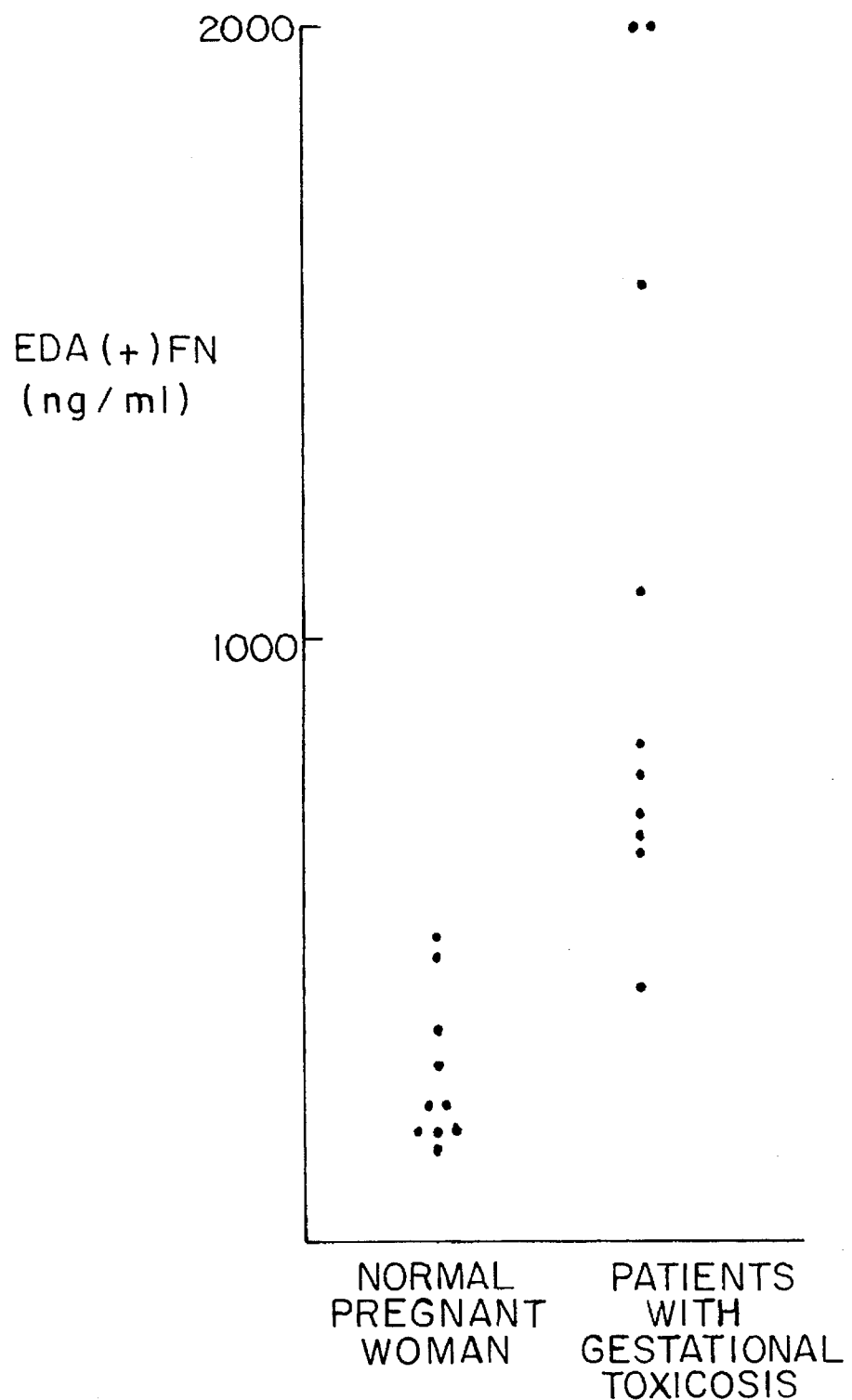
FIG. 4 is a graphic representation of the plasma EDA-FN levels in normal subjects and RA patients as determined in accordance with Example 5, as plotted.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TCTCGGAATT CCATCACCCT CACC    24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGGGAGCTCC GAGCATTGTC ATTC    24

EXAMPLE 6

Determination of Plasma EDA-FN Levels in Patients with Gestational Toxicosis

For 10 normal pregnant women and 10 patients with gestational toxicosis, plasma EDA-FN levels were measured using the monoclonal antibody of the invention in the same manner as in Example 4, for comparison.

We claim:

1. A method for determining the level of EDA-FN in plasma of a patient by an antigen-antibody binding reaction comprising the steps of:

(a) exposing a sample of plasma from a patient to monoclonal antibody HHS-01 produced by hybridoma HHS-01 having Fermentation Research Institute Deposit No. BP-3297, wherein said monoclonal antibody is obtained by using a fused protein derived from a peptide having the amino acid sequence of the EDA region of fibronectin and protein A as an immunogen;

(b) reacting the product of (a) with a labeled anti-FN second monoclonal antibody;

(c) detecting the level of EDA-FN by determining the optical density of the product of (b) as to whether said monoclonal antibody HHS-01 has bound EDA-FN antigen in the plasma of said patient, wherein elevated levels of EDA-FN are indicative of a EDA-FN-associated inflammatory disease selected from the group consisting of vasculitis, thrombosis, gestational toxicosis, renal failure rheumatoid arthritis and diabetes mellitus.

2. The method for determining of claim 1, wherein the inflammatory disease is rheumatoid arthritis.

3. The method for determining of claim 1, wherein the disease is gestational toxicosis.

4. An anti-EDA monoclonal antibody HHS-01 produced by hybridoma HHS-01 having Fermentation Research Institute Deposit No. BP-3297, wherein said monoclonal antibody is obtained by using a fused protein derived from a peptide having the amino acid sequence of the EDA region of fibronectin and protein A as an immunogen.

5. A hybridoma HHS-01 having Fermentation Research Institute Deposit No. BP-3297.

\* \* \* \* \*

UNITED STATES PATENT AND TRADEMARK OFFICE
CERTIFICATE OF CORRECTION

PATENT NO. : 5,571,679
DATED : November 5, 1996
INVENTOR(S) : Kiyotoshi Sekiguchi, Kaneji Asakawa, Eiji Sakashita,
Kazuo Hino, Sadahito Shin, Tetsuya Tachikawa, Hisanobu Hirano It is certified that error appears in the above-indentified patent and that said Letters Patent is hereby corrected as shown below:

On the title page: Items

[22] PCT Filed:      March 26, 1992

[86] PCT No.:        PCT/JP92/00363

§ 371 Date:       September 22, 1993

§ 102(e) Date:    September 22, 1993

[87] PCT Pub. No.:   WO 92/17604

PCT Pub. Date:    October 15, 1992

Signed and Sealed this

Fourth Day of March, 1997

Attest:

BRUCE LEHMAN

*Attesting Officer*    Commissioner of Patents and Trademarks